(12) United States Patent
Van et al.

(10) Patent No.: US 7,794,696 B2
(45) Date of Patent: Sep. 14, 2010

(54) BIODEGRADABLE POLYACETALS FOR IN VIVO POLYNUCLEOTIDE DELIVERY

(75) Inventors: Sang Van, San Diego, CA (US); Jiadong Zhou, San Diego, CA (US); Xiaoli Fu, Vista, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 1738 days.

(21) Appl. No.: 10/946,383

(22) Filed: Sep. 21, 2004

(65) Prior Publication Data

US 2005/0080033 A1  Apr. 14, 2005

Related U.S. Application Data

(60) Provisional application No. 60/507,161, filed on Sep. 29, 2003.

(51) Int. Cl.
*A61K 31/74* (2006.01)
(52) U.S. Cl. .................. 424/78.08; 424/78.27
(58) Field of Classification Search .............. 424/78.27
See application file for complete search history.

(56) References Cited

U.S. PATENT DOCUMENTS

| | | | | |
|---|---|---|---|---|
| 5,206,325 | A * | 4/1993 | Hata et al. ............... | 527/305 |
| 5,958,398 | A | 9/1999 | Papisov | |
| 6,331,311 | B1 | 12/2001 | Brodbeck et al. | |
| 6,383,811 | B2 | 5/2002 | Wolff et al. | |
| 6,794,367 | B1 | 9/2004 | Tanida et al. | |
| 6,878,374 | B2 | 4/2005 | Yu et al. | |
| 7,048,925 | B2 | 5/2006 | Van et al. | |
| 2001/0024829 | A1 | 9/2001 | Wolff et al. | |
| 2002/0034532 | A1 | 3/2002 | Brodbeck et al. | |
| 2002/0052335 | A1 | 5/2002 | Rozema et al. | |
| 2002/0160515 | A1 | 10/2002 | Wolff et al. | |
| 2002/0164315 | A1 | 11/2002 | Wolff et al. | |
| 2003/0008009 | A1 | 1/2003 | Trubetskoy et al. | |
| 2003/0215395 | A1 | 11/2003 | Yu et al. | |
| 2004/0097659 | A1 | 5/2004 | Sato et al. | |
| 2004/0166089 | A1 | 8/2004 | Yu et al. | |

FOREIGN PATENT DOCUMENTS

| | | |
|---|---|---|
| EP | 0 949 905 B1 | 7/2001 |
| JP | 11-335269 | 12/1999 |
| JP | 2003-231748 | 8/2003 |
| WO | WO 92/11844 | 7/1992 |
| WO | WO 96/32419 | 10/1996 |
| WO | WO 98/27962 | 7/1998 |
| WO | WO 98/27963 | 7/1998 |
| WO | WO 0003694 | 1/2000 |
| WO | WO 0113723 | 3/2001 |
| WO | WO 0149841 | 7/2001 |
| WO | WO 02/15955 A2 | 2/2002 |
| WO | WO 02/20663 A2 | 3/2002 |
| WO | WO 02/49573 A2 | 6/2002 |
| WO | WO 2004/076557 | 9/2004 |

OTHER PUBLICATIONS

Oupicky et al. Bioconj. Chem. 1999, 10,764-772.*
Ahn, C.H., et al., "Biodegradable poly(ethylenimine) for plasmid DNA delivery," J. Control. Release 80, 273-282 (2002).
Akinc, Akin et al., "Parallel Synthesis and Biophysical Characterization of a Degradable Polymer Library for Gene Delivery," J. Am. Chem. Soc. 2003, 125, 5316-5323.
Brazeau, G.A. et al., "In Vitro Myotoxicity of Selected cationic macrolecules used in non-viral gene therapy," Pharm. Res. 15, 680-684 (1998).
Choksakulnimitr, S., et al., "In vitro cytotoxicity of macromolecules in different cell culture systems," J. Control Release 34, 233-241 (1995).
Chollet et al. "Side-effects of a systemic injection of linear polyethylenimine-DNA complexes." J Gene Med 2002, 4, 84-91.
Escriou et al. "Cationic lipid-mediated gene transfer: effect of serum on cellular uptake and intracellular fate of lipoamine/DNA complexes." Biochim Biophys Acta 1998, 1368, 276-288.
Godbey et al. "Tracking the intracellular path of PEI/DNA complexes for gene delivery." Proc. Natl. Acad. Sci. 1999, 96, 5177-5181.
Kircheis et al. Polyethylenimine/DNA complexes shielded by transferring target gene expression to tumors after systemic application. Gene Ther 2001, 8, 28-40.
Kircheis R, et al. "Design and gene delivery activity of modified polyethylenimines." Adv. Drug Deliv. Rev. 2001, 53, 341-358.
Lim, Y. et al., "A Self-Destroying Polycationic Polymer: Biodegradable Poly(4-hydroxy-L-proline ester)," J. Am. Chem. Soc. 1999, 121, 5633-5639.
Lim, Y. et al., "Biodegradable Polyester, Poly[α-(4-Aminobutyl)-l-Glycolic Acid], as a Non-toxic Gene Carrier," Pharmaceutical Research 17, 811-816 (2000).
Lim, Y. et al., "Development of a Safe Gene Delivery System Using Biodegradable Polymer, Poly[α-(4-aminobutyl)-L-glycolic acid]," J. Am. Chem. Soc. 2000, 122, 6524-6525.
Lim, Y. K., et al.., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc. 123, 2460-2461 (2001).
Lim, Y., et al., "Biodegradable, Endosome Disruptive, and Cationic Network-type Polymer as a High Efficient and Non-toxic Gene Delivery Carrier," Bioconjugate Chem. 13, 952-957 (2002).
Luo, D. & Saltzman, W. M. "Synthetic DNA delivery systems," Nat. Biotechnol. 18, 33-37 (2000).
Lynn, D.M. et al., "Degradable Poly((β-amino esters): Synthesis, Characterization, and Self-Assembly with Plasmid DNA," J. Am. Chem. Soc. 2000, 122, 10761-10768.
Lynn, D.M.; et al., "Accelerated Discovery of Synthetic Transfection Vectors: Parallel Synthesis and Screening of a Degradable Polymer Library," J. Am. Chem. Soc. 123, 8155-8156 (2001).
Mulligan, R. C., "The basic science of gene therapy," Science 260, 926-932 (1993).
Murthy, N., et al., "A Novel Strategy for Encapsulation and Release of Proteins: Hydrogels and Microgels with Acid-Labile Acetal Cross-Linkers," J. Am. Chem. Soc. 124, 12398-12399 (2002).

(Continued)

*Primary Examiner*—Michael G Hartley
*Assistant Examiner*—Melissa Perreira
(74) *Attorney, Agent, or Firm*—Knobbe Martens Olson & Bear LLP (57) ABSTRACT

Degradable complexes comprising a polycation, a polyanion and a polynucleotide are useful for in vivo polynucleotide delivery applications.

14 Claims, 9 Drawing Sheets

OTHER PUBLICATIONS

Murthy, Niren et al., "A macromolecular delivery vehicle for protein-based vaccines: Acid-degradable protein-loaded microgels," PNAS, Apr. 29, 2003, vol. 100, No. 9, 4995-5000.

Ogris et al. "EGylated DNA/transferrin-PEI complexes: reduced interaction with blood components extended circulation in blood and potential for systemic gene delivery." Gene Ther 1999, 6, 595-605.

Oupicky et al., "Effect of Albumin and Polyanion on the Structure of DNA Complexes with Polycation Containing Hydrophilic Nonionic Block,".

Plank et al. "Activation of the complement system by synthetic DNA complexes: a potential barrier for intravenous gene delivery." Hum Gene Ther 1996, 7, 1437-1446.

Tomlinson R, et al. "Polyacetal-doxorubicin conjugates designed for pH-dependent degradation." Bioconjug Chem. 2003, 14(6), 1096-1106.

Tomlinson, R. et al., "Pendent Chain Functionalized Polyacetals That Display pH-Dependent Degradation: A Platform for the Development of Novel Polymer Therapeutics," Macromolecules 35, 473-480 (2002).

Tousignant et al. "Comprehensive analysis of the acute toxicities induced by systemic administration of cationic lipid:plasmid DNA complexes in mice." Hum Gene Ther 2000, 11, 2493-2513.

Trubetskoy et al. Layer-by-layer deposition of oppositely charged polyelectrolytes on the Surface of Condensed DNA particles. Nucleic Acids Res. 1999, 27, 3090-3095.

Trubetskoy et al. "Recharging cationic DNA complexes with highly charged polyanions for in vitro and in vivo gene delivery." Gene Ther. 2003, 10, 261-271.

Tuominen, J. et al., "Biodegradation of Lactic Acid Based Polymers under Controlled Composting Conditions and Evaluation of the Ecotoxicological Impact," Biomacromolecules 3, 445-455 (2002).

Wagner, Ernst, "Strategies to Improve DNA Polyplexes for in Vivo Gene Transfer: Will "Artificial Viruses" Be the Answer?" Pharmaceutical Research, vol. 21, No. 1, Jan. 2004, 8-14.

U.S. Appl. No. 10/651,394, filed Aug. 28, 2003.

International Search Report for International Application No. PCT/US2004/030323 mailed on Feb. 2, 2005.

Ahn, Cheol-Hee et al., "Biodegradable poly(ethylenimine) for plasmid DNA delivery," *Journal of Controlled Release*, vol. 80, pp. 273-282, 2002.

Basko, Malgorzata, et al., "Synthesis of Double Hydrophilic Graft Copolymers with a Polyacetal Backbone," *Macromolecules*, vol. 35, pp. 8948-8953, 2002.

Brazeau, Gayle A., et al., "In Vitro Myotoxicity of Selected Cationic Macromolecules Used in Non-Viral Gene Delivery," *Pharmaceutical Research*, vol. 15, No. 5, pp. 680-684, 1998.

Capan, Yilmaz, et al., Preparation and Characterization of Poly(D,L-Lactide-Co-Glycolide) Microspheres for Controlled Release of Poly (L-Lysine) Complexed Plasmid DNA, *Pharmaceutical Research*, vol. 16, No. 4, pp. 509-513, 1999.

Carpino, Louis A., et al., "The 9-Fluorenylmethoxycarbonyl Amino-Protecting Group," *J. Org. Chem.*, vol. 37, No. 22, pp. 3404-3409, 1972.

Choksakulnimitr, Suthummar, et al., "In vitro cytotoxicity of macromolecules in different cell culture systems," *Journal of Controlled Release*, vol. 34, pp. 233-241, 1995.

Derosa, Giuseppe, et al., Poly (lactide-*co*-glycolide) Microspheres for the Controlled Release of Oligonucleotide/Polyethylenimine Complexes, *Journal of Pharmaceutical Sciences*, vol. 91, No. 3, pp. 790-799, 2002.

Godbey, W.T., et al., "Size matters: Molecular weight affects the efficiency of poly(ethylenimine) as a gene delivery vehicle," *Journal of Biomedical Materials Research* Part A, vol. 45, pp. 268-275, 1999.

Lim, Yong-beom et al., "Biodegradable, Endosome Disruptive, and Cationic Network-type Polymer as a Highly Efficient and Nontoxic Gene Delivery Carrier," *Bioconjugate Chem.*, vol. 13, No. 5, pp. 952-957, 2002.

Lim, Yong-beom, et al., "Biodegradable Polyester, Poly[α-(4-Aminobutyl)-L-Glycolic Acid], as a Non-Toxic Gene Carrier," *Pharmaceutical Research*, vol. 17, No. 7, pp. 811-816, 2000.

Lim, Yong-beom et al., "Cationic Hyperbranched Poly(amino ester): A Novel Class of DNA Condensing Molecule with Cationic Surface, Biodegradable Three-Dimensional Structure, and Teriary Amine Groups in the Interior," *Journal of American Chemical Society*, vol. 123, No. 10, pp. 2460-2461, 2001.

Luo, Dan, et al., "Synthetic DNA delivery systems," *Nature Biotechnology*, vol. 18, pp. 33-37, 2000.

Lynn, David M., et al., "Accelerated Discovery of Synthetic Transfection Vectors: Parallel Synthesis and Screening of a Degradable Polymer Library," *Journal American Chemical Society*, vol. 123, No. 33, pp. 8155-8156, 2001.

Mulligan, Richard C., "The Basic Science of Gene Therapy," *Science*, vol. 260, pp. 926-932, 1993.

Murthy, Niren, et al., "A Novel Strategy for Encapsulation and Release of Proteins: Hydrogels and Microgels with Acid-Labile Acetal Cross-Linkers," *Journal American Chemical Society*, vol. 124, No. 42, pp. 12398-12399, 2002.

Tomlinson, Ryan, et al., "Pendent Chain Functionalized Polyacetals That Display pH-Dependent Degradation: A Platform for the Development of Novel Polymer Therapeutics," *Macromolecules*, vol. 35, No. 2, pp. 473-480, 2002.

Tomlinson, Ryan, et al., "Polyacetal-Doxorubicin Conjugates Designed for pH-Dependent Degradation," *Bioconjugate Chem.*, vol. 14, pp. 1096-1106, 2003.

Torres, Lennard F., et al., "A New Polymerization System for Bicyclic Acetals: Toward the Controlled/'Living' Cationic Ring-Opening Polymerization of 6.8-Dioxabicyclo[3.2.1]octane," *Macromolecules*, vol. 32, No. 21, pp. 6958-6962, 1999.

Trubetskoy, VS, et al., "Recharging Cationic DNA Complexes With Highly Charged Polyanions for In Vitro and In Vivo Gene Delivery", *Gene Therapy*, vol. 10, pp. 261-271, 2003.

Tuominen, Jukka, et al., "Biodegradation of Lactic Acid Based Polymers under Controlled Composting Conditions and Evaluation of the Ecotoxicological Impact," *Biomacromolecules*, vol. 3, No. 3, pp. 445-455, 2002.

International Preliminary Report of Patentability dated Sep. 9, 2005 for International Application No. PCT/US2004/005363, filed Feb. 24, 2004.

International Search Report and Written Opinion dated Jul. 12, 2004 for International Application No. PCT/US2004/005363, filed Feb. 24, 2004.

International Preliminary Report of Patentability dated Apr. 13, 2006 for International Application No. PCT/US2004/030323, filed Sep. 16, 2004.

International Search Report and Written Opinion dated Feb. 2, 2005 for International Application No. PCT/US2004/030323, filed Sep. 16, 2004.

Murthy, Niren et al., "Design and synthesis of pH-responsive polymeric carriers that target uptake and enhance the intracellular delivery of oligonucleotides" Journal of Controlled Release, 2003, pp. 365-374, vol. 89, No. 3.

* cited by examiner

BIODEGRADABLE POLYACETALS FOR IN VIVO POLYNUCLEOTIDE DELIVERY

RELATED APPLICATION INFORMATION

This application claims priority to U.S. Provisional Patent Application No. 60/507,161, filed Sep. 29, 2003, which is hereby incorporated by reference in its entirety.

BACKGROUND OF THE INVENTION

1. Field of the Invention

This invention relates generally to degradable polymer compositions useful for in vitro and in vivo polynucleotide delivery applications. More particularly, this invention relates to degradable complexes comprising polyanions, polycations and polynucleotides useful for in vivo polynucleotide delivery applications in mammals.

2. Description of the Related Art

There is a need for non-viral drug delivery systems having desirable properties such as low immunogenicity, amenable to production on a relatively large scale, and which can be easily modified to provide a range of biological properties. See Mulligan, R. C., "The basic science of gene therapy," Science 260, 926-932 (1993); and Luo, D. & Saltzman, W. M. "Synthetic DNA delivery systems," Nat. Biotechnol. 18, 33-37 (2000). However, non-degradable cationic polymers such as poly(lysine) and polyethyleneimine (PEI) can have significant cytotoxicity. See Choksakulnimitr, S., Masuda, S., Tokuda, H., Takakura, Y. & Hashida, M., "In vitro cytotoxicity of macromolecules in different cell culture systems," J. Control Release 34, 233-241 (1995); Brazeau, G. A., Attia, S., Poxon, S. & Hughes, J. A., "In Vitro Myotoxicity of Selected cationic macrolecules used in non-viral gene therapy," Pharm. Res. 15, 680-684 (1998); and Ahn, C.-H., Chae, S. Y., Bae, Y. H. & Kim, S. W. "Biodegradable poly(ethylenimine) for plasmid DNA delivery," J. Control. Release 80, 273-282 (2002).

To reduce cytotoxicity, some efforts have been made to develop degradable cationic polymers (polycations). See Ahn, C.-H., Chae, S. Y., Bae, Y. H. & Kim, S. W., "Biodegradable poly(ethylenimine) for plasmid DNA delivery," J. Control. Release 80, 273-282 (2002); Lynn, D. M.; Anderson, D. G.; Putman, D.; Langer, R., "Accelerated Discovery of Synthetic Transfection Vectors: Parallel Synthesis and Screening of a Degradable Polymer Library," J. Am. Chem. Soc. 123, 8155-8156 (2001); Lim, Y. et al., "Biodegradable Polyester, Poly[α-(4-Aminobutyl)-l-Glycolic Acid], as a Non-toxic Gene Carrier," Pharmaceutical Research 17, 811-816 (2000); Lim, Y., Kim, S., Suh, H. & Park, J.-S., "Biodegradable, Endosome Disruptive, and Cationic Network-type Polymer as a High Efficient and Non-toxic Gene Delivery Carrier," Bioconjugate Chem. 13, 952-957 (2002); Lim, Y. K., S.; Lee, Y.; Lee, W.; Yang, T.; Lee, M.; Suh, H.; Park, J., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc. 123, 2460-2461 (2001); and Tuominen, J. et al., "Biodegradation of Lactic Acid Based Polymers under Controlled Composting Conditions and Evaluation of the Ecotoxicological Impact," Biomacromolecules 3, 445-455 (2002). However, under physiological conditions, these cationic polymers are susceptible to degradation via base-catalyzed hydrolysis.

Acid-sensitive polymers containing acetal linkages have been reported, see Tomlinson, R. et al., "Pendent Chain Functionalized Polyacetals That Display pH-Dependent Degradation: A Platform for the Development of Novel Polymer Therapeutics," Macromolecules 35, 473-480 (2002); and Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers," J. Am. Chem. Soc. 124, 12398-12399 (2002).

Additional References:

Kircheis R, Wightman L, Wagner E. "Design and gene delivery activity of modified polyethylenimines." Adv. Drug Deliv. Rev. 2001, 53, 341-358.

Godbey et al. "Tracking the intracellular path of PEI/DNA complexes for gene delivery." Proc. Natl. Acad. Sci. 1999, 96, 5177-5181.

Chollet et al. "Side-effects of a systemic injection of linear polyethylenimine-DNA complexes." J Gene Med 2002, 4, 84-91.

Tousignant et al. "Comprehensive analysis of the acute toxicities induced by systemic administration of cationic lipid:plasmid DNA complexes in mice." Hum Gene Ther 2000, 11, 2493-2513.

Escriou et al. "Cationic lipid-mediated gene transfer: effect of serum on cellular uptake and intracellular fate of lipoamine/DNA complexes." Biochim Biophys Acta 1998, 1368, 276-288.

Plank et al. "Activation of the complement system by synthetic DNA complexes: a potential barrier for intravenous gene delivery." Hum Gene Ther 1996, 7, 1437-1446.

Ogris et al. "EGylated DNA/transferrin-PEI complexes: reduced interaction with blood components extended circulation in blood and potential for systemic gene delivery." Gene Ther 1999, 6, 595-605.

Kircheis et al. "Polyethylenimine/DNA complexes shielded by transferring target gene expression to tumors after systemic application." Gene Ther 2001, 8, 28-40.

Trubetskoy et al. "Layer-by-layer deposition of oppositely charged polyelectrolytes on the Surface of Condensed DNA particles." Nucleic Acids Res. 1999, 27, 3090-3095.

Trubetskoy et al. "Recharging cationic DNA complexes with highly charged polyanions for in vitro and in vivo gene delivery." Gene Ther. 2003, 10, 261-271.

U.S. patent application Ser. No. 10/270,788, filed Oct. 11, 2002 (published as U.S. Patent Publication No. 2003-0215395 A1), and U.S. Provisional Patent Application Ser. No. 60/378,164, filed May 14, 2002.

U.S. patent application Ser. No. 10/375,705, filed Feb. 25, 2003 (published as U.S. Patent Publication No. 2004-0166089 A1).

Tomlinson R, Heller J, Brocchini S, Duncan R. "Polyacetal-doxorubicin conjugates designed for pH-dependent degradation." Bioconjug Chem. 2003, 14(6), 1096-1106.

SUMMARY OF THE INVENTION

Figure 6:
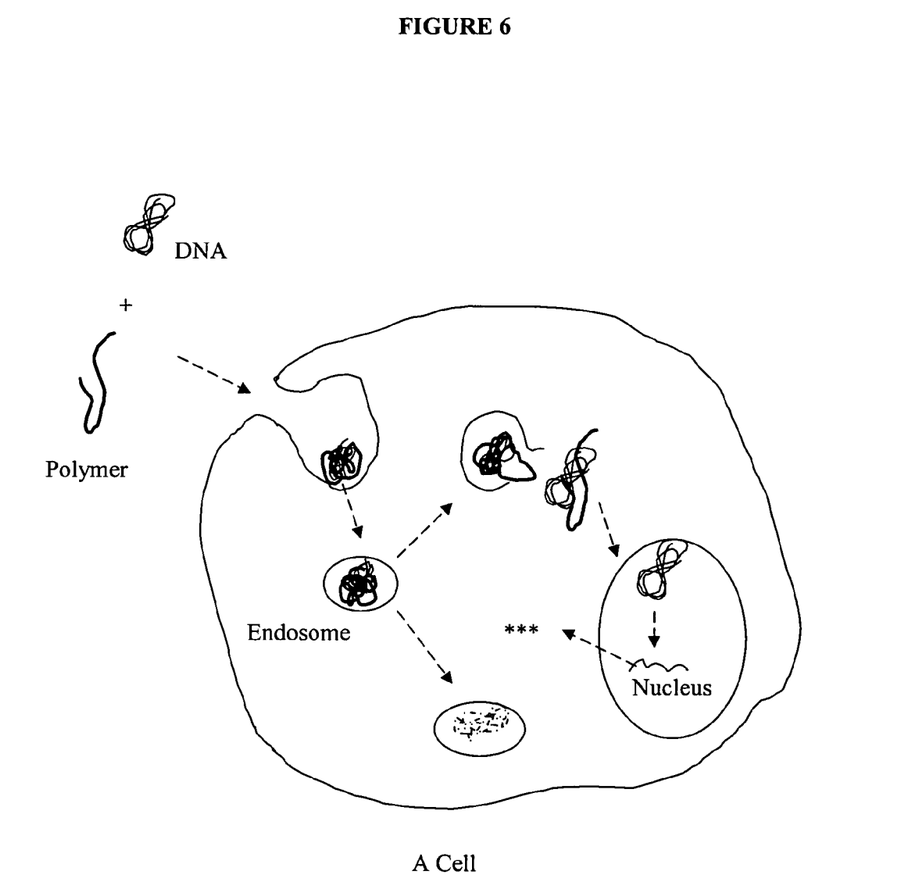
FIG. 6 schematically illustrates an endocytoxic pathway for the entry of a binary polycation-DNA complex into a cell.
Figure 7:
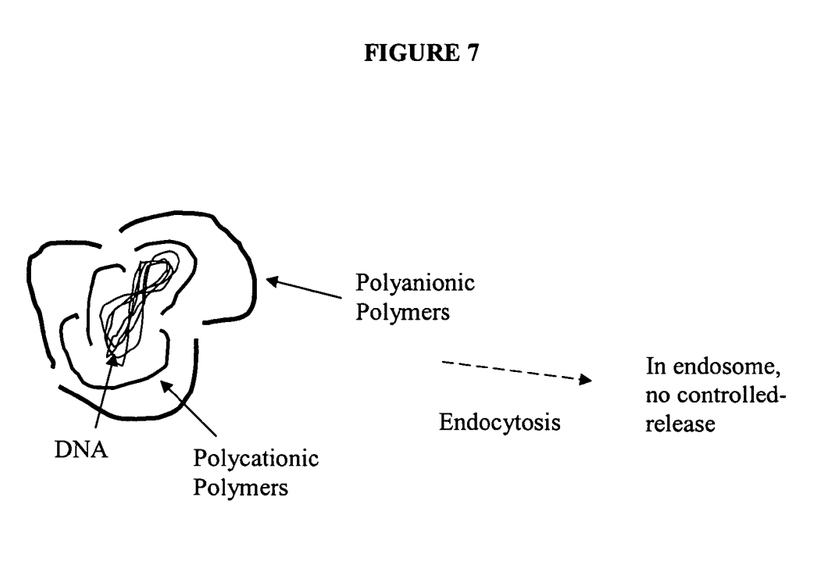
FIG. 7 schematically illustrates a tertiary complex of polyanion, polycation and polynucleotide.

It is believed that binary polycation-DNA complexes enter cells by an endocytotic pathway as illustrated in FIG. 6. However, it has been found that the ability of such binary complexes to deliver polynucleotides to cells in vivo is limited by toxicity and low gene expression. It is believed that decreased transfection efficiency in vivo is caused by interaction of the positively charged binary polycation-DNA complexes with negatively charged components such as proteins. The positive charges of the binary polycation-DNA complex can be shielded by treatment with polyethyleneglycol (PEG) or proteins such as transferrin, or tertiary complexes may be formed with polycations as shown in FIG. 7. However, in practice it has been found that such additional components tend to complicate the release and delivery of the DNA.

Figure 8:
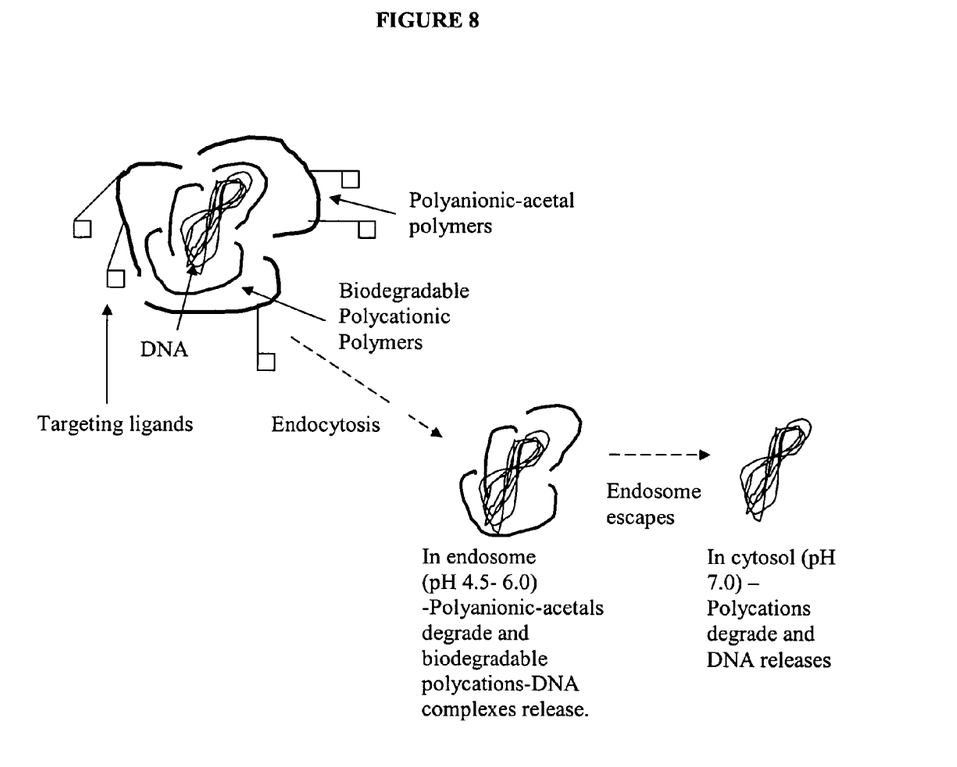
FIG. 8 schematically illustrates a biodegradable tertiary complex of polyanion, polycation and polynucleotide.

It has now been found that biodegradable tertiary complexes comprising a polyanion, a polycation and a polynucleotide, as shown in FIG. 8, provide a number of benefits. Thus, a preferred embodiment provides a complex for delivering a polynucleotide to a cell, comprising a polynucleotide; a polycation; and an acid-degradable polyanion.

Another preferred embodiment provides a method of making such a complex, comprising intermixing a first solution comprising the acid-degradable polyanion with a second solution comprising the polycation and the polynucleotide.

Another preferred embodiment provides a method of delivering such a complex into a cell, comprising contacting the complex with the cell.

These and other embodiments are described in greater detail below.

BRIEF DESCRIPTION OF THE DRAWINGS

These and other aspects of the invention will be readily apparent from the following description and from the appended drawings, which are meant to illustrate and not to limit the invention, and wherein.

DETAILED DESCRIPTION OF THE PREFERRED EMBODIMENTS

A preferred embodiment is directed to a tertiary complex comprising a polyanion, a polycation and a polynucleotide, wherein at least one of the polyanion and the polycation is biodegradable (e.g., acid-degradable). Preferably, the polycation is biodegradable and the polyanion is acid-degradable as illustrated in FIG. 8. Preferably, the polynucleotide is DNA or RNA. Non-limiting examples of preferred polynucleotides include plasmid DNA, antisense DNA, DNA oligomer, siRNA, ribozyme, and tetramer.

Polycations are macromolecules with multiple groups that are positively charged or capable of being positively charged under physiological or acidic conditions. A quaternary amine is an example of a cationic group; primary, secondary and tertiary amines are examples of groups that are capable of being positively charged under physiological or acidic conditions. Examples of polycations include polyamine and poly (ethylenimine). The polycation is typically associated with a counterion such as a negatively charged group on a polyanion, an organic ion, or an inorganic ion such as fluoride, chloride, bromide, iodide, nitrate, or sulfate. Preferred biodegradable polycations comprise one or more degradable recurring units that undergo degradation under physiological conditions, preferably resulting in scission of the polycation backbone to form lower molecular weight fragments. Non-limiting examples of preferred degradable recurring units include ester, amide, phosphatediester, acetal, imine, hydrazone, enol, enol ether, enamine, ketal, and oxime. Non-limiting examples of preferred biodegradable polycations thus include polyester-polyamine, polyphosphatediester-polyamine, and polyacetal-polyamine. Biodegradable polycations may be purchased from commercial sources or prepared by methods known to those skilled in the art. Preferred polycations are preferably prepared as described in U.S. patent application Ser. No. 10/270,788, filed Oct. 11, 2002 (published as U.S. Patent Publication No. 2003-0215395 A1), and U.S. Provisional Patent Application Ser. No. 60/378,164, filed May 14, 2002, both of which are hereby incorporated by reference in their entireties and particularly for the purpose of describing the preparation of degradable polycations. The molecular weight of polycations is preferably in the range of about 500 daltons to about 5,000,000 daltons, more preferably in the range of about 2,000 daltons to about 50,000 daltons.

Figure 3:
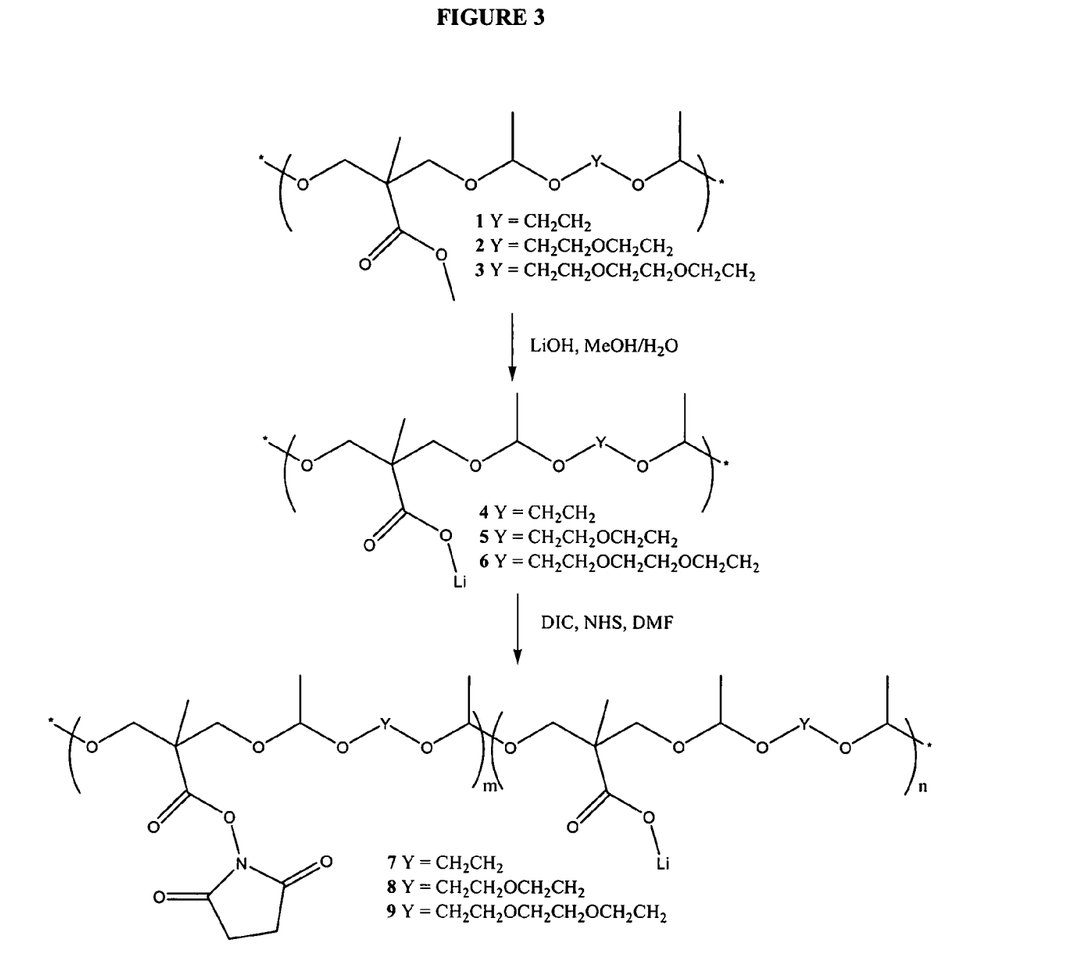
FIG. 3 shows a preferred reaction scheme for the preparation of anionic polyacetals 4-9.
Figure 4:
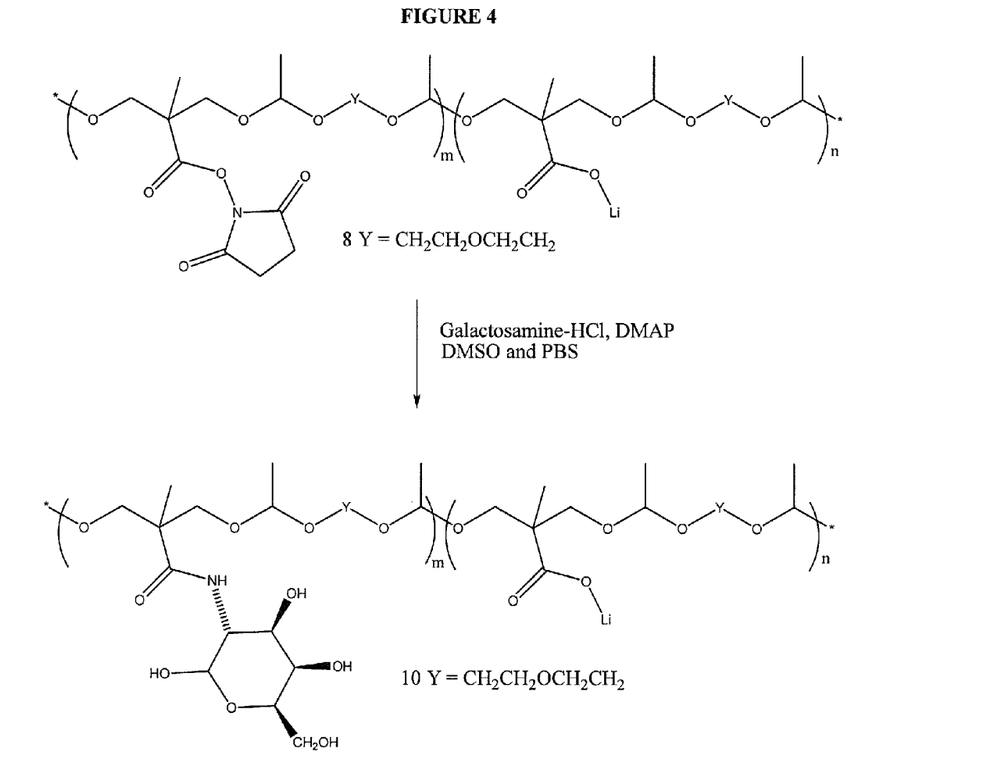
FIG. 4 shows a preferred reaction scheme for the preparation of anionic polyacetal 10.

Polyanions are macromolecules with multiple groups that are negatively charged. Carboxylate ($CO_2^-$), sulfonate ($SO_3^-$), and phosphate ($PO_3^-$) are non-limiting examples of groups that are negatively charged. The polyanion is typically associated with a counterion such as a cationic group on a polycation, an ammonium ion ($NH_4^+$), or a metal ion such as $Li^+$, $Na^+$, $K^+$, $Rb^+$, $Cs^+$, $Be^{2+}$, $Mg^{2+}$, or $Ca^{2+}$. Preferred biodegradable polyanions comprise one or more degradable recurring units that undergo degradation under physiological conditions, preferably resulting in scission of the polycation backbone to form lower molecular weight fragments. Preferred biodegradable polyanions are acid-degradable. Non-limiting examples of preferred degradable recurring units include ester, amide, phosphatediester, acetal, imine, hydrazone, enol, enol ether, enamine, ketal, and oxime. Biodegradable polyanions may be purchased from commercial sources or prepared by methods known to those skilled in the art. Preferred polyanions are polyacetals prepared by hydrolysis of the corresponding polyacetal esters as illustrated in FIG. 3. The polyacetal esters are preferably prepared as described in U.S. patent application Ser. No. 10/375,705, filed Feb. 25, 2003 (published as U.S. Patent Publication No. 2004-0166089 A1), which is hereby incorporated by reference in its entirety and particularly for the purpose of describing the preparation of degradable polyacetals. The molecular weight of polyanions is preferably in the range of about 500 to about 5,000,000.

In particularly preferred embodiments, biodegradable polyanions comprise a targeting ligand, preferably a targeting ligand selected from the group consisting of galactose, lactose, mannose, peptide, antibody, antibody fragment, and transferrin. Particularly preferred polyanions comprise recurring units represented by Formula (1):

Ser. No. 10/375,705, filed Feb. 25, 2003 (published as U.S. Patent Publication No. 2004-0166089 A1), which has been incorporated by reference herein as discussed above.

Biodegradable tertiary complexes comprising a polyanion, a polycation and a polynucleotide may be prepared in various ways. Preferably, the polyanion, polycation and polynucleotide are dissolved in solution and intermixed to form a tertiary complex. More preferably, a the polycation and the polynucleotide are intermixed in solution, preferably forming a positively charged binary complex, and the resulting solution is then preferably intermixed with the polyanion to form a tertiary complex. The ratios of polycation to polynucleotide (I)

wherein Y is selected from the group consisting of —(CH$_2$)$_2$—, —(CH$_2$)$_2$—O—(CH$_2$)$_2$—, and —(CH$_2$)$_2$—O—(CH$_2$)$_2$—O—(CH$_2$)$_2$—; wherein W is a targeting ligand selected from group consisting of galactose, lactose, mannose, transferrin, antibody, antibody fragment, and RGD peptide; wherein m and n are each individually integers in the range of 1 to 100,000; and wherein Z is selected from the group consisting of Li, Na, K, Rb, Cs, Be, Mg, and Ca. For example, a highly preferred polyanion comprises recurring units represented by formula (II)

and polyanion to polynucleotide may vary over a broad range. Preferably, the ratio of polycation to polynucleotide is in the range of about 1:1 to about 100:1, more preferably in the range of about 5:1 to 50:1.

The ratio of polyanion to polynucleotide is preferably selected by taking into consideration the polycation to polynucleotide ratio, and utilizing an amount of polyanion that is effective to at least partially neutralize any excess of cationicity present in a binary complex formed between the polycation and polynucleotide. For example, the amount of poly- (II)

wherein Y is selected from the group consisting of —(CH$_2$)$_2$—, —(CH$_2$)$_2$—O—(CH$_2$)$_2$—, and —(CH$_2$)$_2$—O—(CH$_2$)$_2$—O—(CH$_2$)$_2$—; wherein m and n are each individually integers in the range of one to 100,000; and wherein Z is selected from the group consisting of Li, Na, K, Rb, Cs, Be, Mg, and Ca. A polyanion comprising recurring units represented by formula (II) is preferably prepared by hydrolyzing the corresponding polyacetal precursor to form a hydrolyzed polyacetal; and coupling a galactosamine with the hydrolyzed polyacetal to form the polyanion. The coupling is preferably conducted using a coupling reagent selected from the group consisting of 1,3-diisopropylcarbodiimide (DIC), N-hydroxysuccinimide (NHS), and 4-dimethylaminopyridine (DMAP). The polyacetal precursor is preferably prepared as described in U.S. patent application cation is preferably in excess of the amount of polynucleotide on a weight basis, and thus the amount of cationic charge on the polycation is often in excess of the amount of negative charge on the polynucleotide. Thus, any binary complex formed by using such amounts of polycation and polynucleotide will typically have a net positive charge. Preferably, the amount of polyanion used with such amounts of polycation and polynucleotide is effective to at least partially neutralize the net positive charge. More preferably, the polyanion is used in an amount that slightly exceeds the amount effective to neutralize the net positive charge. Those skilled in the art recognize that the relative amounts of polycation, polyanion and polynucleotide needed to obtain a tertiary complex having the desired nucleotide content and charge level may be calculated in advance based on the known or determined charge levels of the components, and thus formation of a binary polycation-polynucleotide complex is not required prior to the addition of the polyanion.

In vitro and in vivo delivery of the polynucleotide to the interior of a cell (transfection) may be carried out by contacting the tertiary complex with the cell to be transfected. Preferably, the cell is a mammalian cell. The contacting of the tertiary complex with the cell in vitro may be carried out in various ways known to those skilled in the art, e.g., as described in the non-limiting examples set forth below. Contacting of the tertiary complex with the cell in vivo is preferably carried out by introducing the complex into the body of an animal, preferably a mammal, e.g., by systemic or local administration. Preferably, administration is conducted by identifying a mammal, e.g., a human, having cells in need of transfection with a particular polynucleotide, then administering a tertiary complex comprising the polynucleotide to the mammal in an amount effective to deliver the desired amount of polynucleotide to the cells. Such amounts of the tertiary complex effective to deliver desired polynucleotide may be determined by routine in vitro experimentation and/or by other methods known to those skilled in the art, e.g., clinical trials.

EXAMPLES

Cell lines and cultures used in the following examples were prepared as follows: Hepatoma (HepaG2) cells were grown in Dulbecco's-modified Eagle's medium (DMEM) containing 10% (v/v) heat-inactivated fetal bovine serum (FBS), 100 U/ml Penicillin and 100 µg/ml streptomycin, and incubated at 37° C. at 100% humidity atmosphere containing 7.5% $CO_2$. The plasmid vector pCMV-luc was constructed by cloning the firefly luciferase gene into pCMV-0, with the same backbone of mammalian expression vector. The plasmid was expanded in DH5α *E. coli* and purified with Qiagen Plasmid Max Preparation Kit according to the manufacture's instructions. The quantity and quality of the purified plasmid DNA was assessed by spectrophotometric analysis at 260 and 280 nm as well as by electrophoresis in 0.8% agarose gel. Purified plasmid DNA was resuspended in sterile distilled, deionized $H_2O$ and frozen. Polyacetals 1-3 and biodegradable polycation 12 were synthesized in the manner described in U.S. patent application Ser. No. 10/270,788, filed Oct. 11, 2002 (published as U.S. Patent Publication No. 2003-0215395 A1); U.S. Provisional Patent Application Ser. No. 60/378, 164, filed May 14, 2002; and U.S. patent application Ser. No. 10/375,705, filed Feb. 25, 2003 (published as U.S. Patent Publication No. 2004-0166089 A1). All of the chemicals and reagents for syntheses of polyacetals and biodegradable polycations were purchased from commercial sources. Poly(ethylenimine)-600 daltons (PEI-600) was purchased from Polysciences, Inc. Polymer molecular weights were measured by aqueous high pressure size exclusion chromatography (HPSEC) using polyethylene glycol standards. Sizes and zeta potentials of binary and tertiary complexes were analyzed by ZetaPALS (zeta potential and particle size analyzer) by following the protocols provided by the manufacturer (Brookhaven Instruments Corporation) Buffers and PEI (branched, 25 k Daltons, Sigma-Aldrich) were obtained commercially.

Examples 1-3

Synthesis of polyacetals 4-6 (FIG. 3): The following description for the synthesis of anionic polyacetal 5 is illustrative: A solution of lithium hydroxide monohydrate (0.45 g, 10.7 mmol) in methanol/water (1:1) (20 mL) was added to polyacetal 2 (2.57 g, 8.6 mmol). The reaction mixture was stirred for 24 hours and concentrated by rotary evaporation. The residue was redissolved in ethanol (50 mL). Acetone (200 mL) was added to the resulting solution to form a precipitate. The mixture was decanted and the residue was placed under high vacuum to give polyanion 5 (1.7 g).

Examples 4-6

Synthesis of polyacetals 7-9 (FIG. 3): The following description for the synthesis of polyacetal 8 is illustrative: A solution of 1,3-diisopropylcarbodiimide (DIC, 0.082 g, 0.65 mmol) in DMF (10 mL) was added to anionic polyacetal 5 (0.39 g, 1.3 mmol). N-hydroxysuccinimide (NHS, 0.075 g, 0.65 mmol) in DMF (15 mL) was added into the reaction mixture. The reaction was stirred for 7 hours. The precipitate was isolated and washed with more DMF and placed under high vacuum to give 8 (0.45 g).

Example 7

Synthesis of polyacetal 10: A solution of galactosamine-HCl (0.11 g, 0.51 mmol) and 4-dimethylaminopyridine (DMAP, 0.12 g, 0.98 mmol) in dimethylsulfoxide (DMSO, 2 mL) was added to a solution of polyanion 8 (0.20 g) in PBS (8 mL). The reaction mixture was stirred for 15 hours. The reaction solution was added with acetone (200 mL) and stirred. Within 1 hour, precipitate formed. The precipitate was redissolved in distilled water (2 mL) and dialyzed in distilled water (2000 mL) for 5 hours. The solution was placed under high vacuum to give 10.

Example 8

Figure 5:
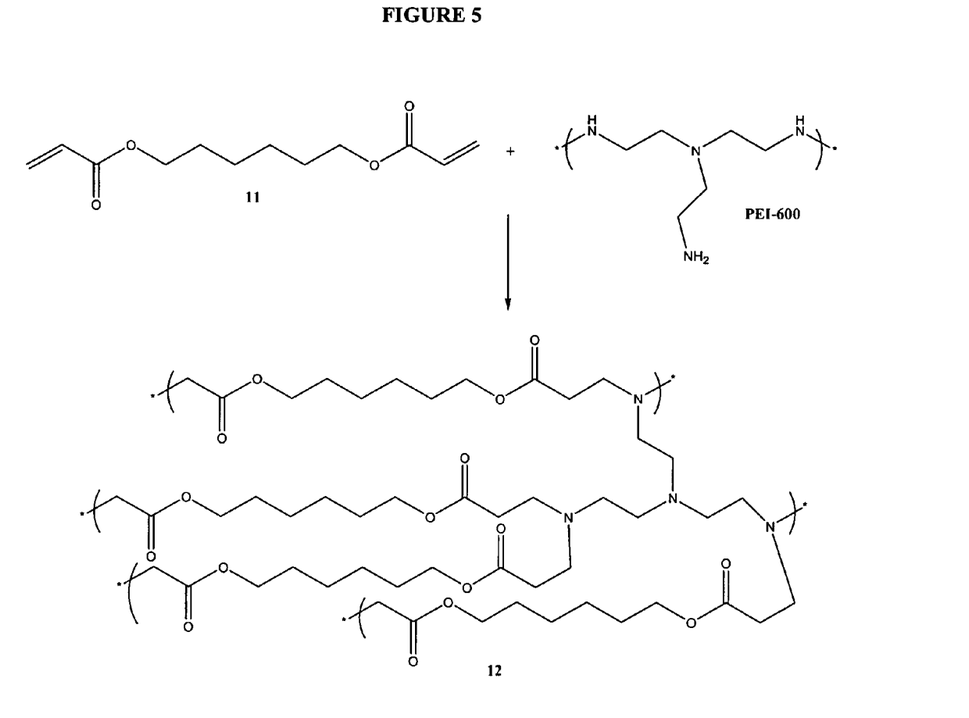
FIG. 5 shows a preferred reaction scheme for the preparation of biodegradable polycation 12.

The polycation 12 used in the following examples was prepared as described in U.S. Ser. No. 10/270,788, filed Oct. 11, 2002 (published as U.S. Patent Publication No.2003-0215395 A1), and U.S. No. 60/378,164, filed May 14, 2002, as illustrated in FIG. 5.

Example 9

Figure 1:
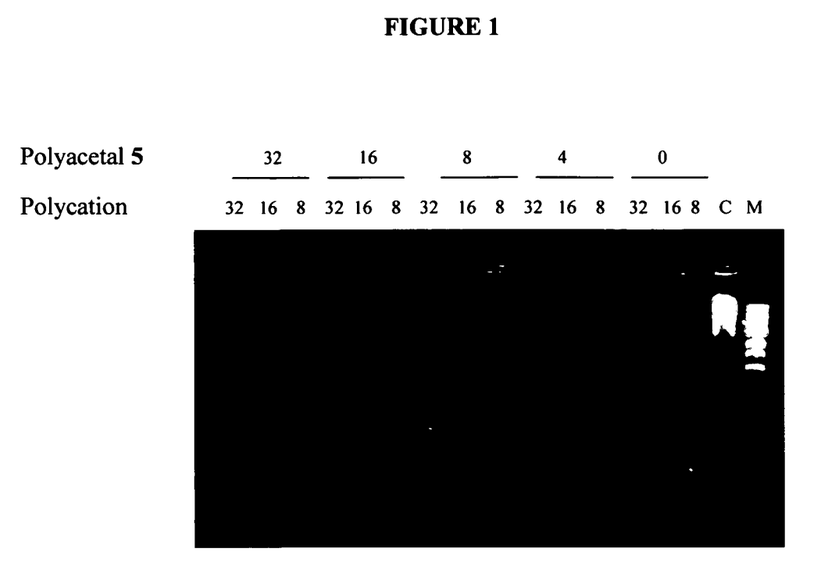
FIG. 1 shows a reproduction of a photograph showing the results of a retardation assay carried out using complexes formed from an acid degradable polyanion (polyacetal 5), a biodegradable polycation and DNA. The numbers above the photograph indicate the ratios of polycation to DNA and polyanion to DNA ratio (by weight/weight). The results show that, for this particular set of conditions, DNA was not released from the complex, as compared to a control C (no polymers) and a molecular marker M. The results show that acid degradable polyanion (polyacetal 5), biodegradable polycation and DNA formed a tertiary complex.

Tertiary complexation of polyacetal 5 to form DNA/polycation complexes: Samples of plasmid DNA and biodegradable polycation 12 were diluted in Optimem solution (Life Technologies) and mixed to form a series of binary polycation/DNA complexes having polycation to DNA ratios ranging from 32:1 to 8:1 by weight. After about 15 minutes, a solution of polyanion 5 in Optimem solution was added into the polycation/DNA complexes and incubated at room temperature for another 15 minutes. The resulting tertiary complexes were added to agarose gel and electrophoresis was performed: Five gl of loading dye was added to each sample, and 15 µl of each sample were loaded per well. The tertiary complexes were analyzed by electrophoresis in a 0.3% agarose gel with 0.04 M Tris-acetate buffer, pH 7.4, containing 1 mM EDTA, at 100V for 30 minutes. The tertiary complexes were visualized by UV illumination. The retardation assay results for the tertiary polycation/polyanion/DNA complexes are shown in FIG. 1. The results indicate that the tertiary complexes were successfully formed and that polyanion 5 did not compete with DNA, so that DNA was released from the tertiary complexes at each of the ratios.

Example 10

In vitro transfection using a tertiary complex comprising polycation 12 and anionic polyacetal 10 was carried out as follows: HepaG2 cells were plated in 24-well tissue culture plates ($2\times10^5$ cells/well for HepaG2 cells) and incubated overnight in DMEM with 10% fetal bovine serum (FBS). For each well, a 20 µl aliquot of polycation 12 solution (each containing a different dose of biodegradable polycation 12) was added dropwise into a 20-µl DNA solution containing 0.6 µg of plasmid DNA (pCMV-GFP plasmid DNA or pCMV-luc), while vortexing. Dropwise addition while vortexing was found to be highly preferable, because it was found that transfection results depended on the mixing conditions. The solutions containing DNA and polycation 12 were incubated for 15 min at room temperature to form binary DNA-polycation 12 complexes. Then 20 ml of solutions containing anionic polyacetal 10 were added to each of the binary DNA-polycation 12 complexes to form tertiary complexes (containing DNA, anionic polyacetal 10, and polycation 12). Next, 60 mL samples of these tertiary complexes were added into each well and the cells were incubated (37° C., 7.5% $CO_2$) for 24 hours. After that incubation, fruitfly luciferase activities were detected as described below.

Figure 2:
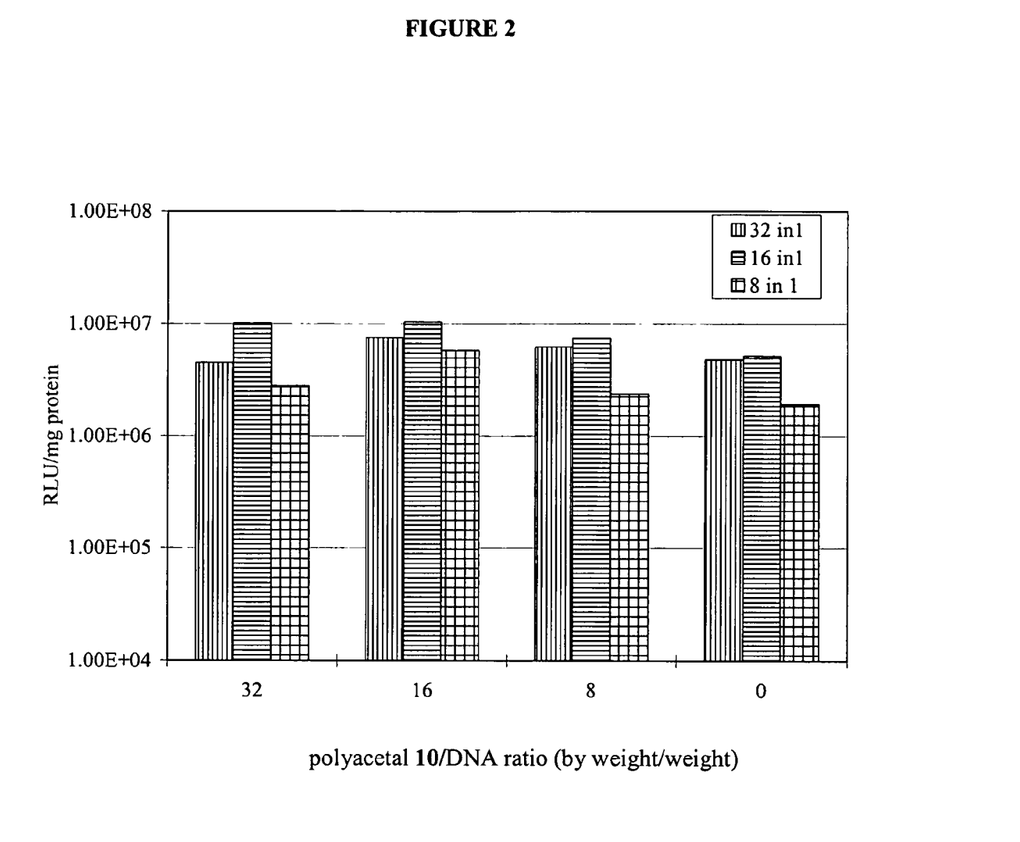
FIG. 2 shows a bar graph plotting Relative Light Units (RLU) per milligram of protein for transfection of HepaG2 cells using a tertiary complex formed from an acid degradable polyanion (polyacetal 10), a biodegradable polycation, and DNA, as compared to a binary complex formed from the biodegradable polycation and DNA, without the anionic polymer. The results show that transfection using the tertiary complex was superior to transfection using the binary complex. The results indicate that the tertiary complex is likely to be effective for in vivo polynucleotide delivery. Labeling: Ratio of biodegradable polycation:DNA (by weight/weight) for vertical line bar is 32:1, horizontal line bar is 16:1, and grid line bar is 8:1. The numbers on the horizontal axis are the ratio of polyacetal 10 to DNA (by weight/weight).

Luciferase activity was measured using a chemiluminescent assay following the manufacturer's instructions (Luciferase Assay System, Promega, Madison, Wis., USA). About twenty four hours after the transfections described above, the cells were rinsed twice with PBS and then were lysed with lysis buffer (1% Triton X-100, 100 mM $K_3PO_4$, 2 mM dithiothreitol, 10% glycerol, and 2 mM EDTA pH 7.8) for 15 min at room temperature. A 10-µl aliquot of cell lysate was then mixed with 50-µl of luciferase assay reagent with the injector at room temperature in the luminometer. Light emission was measured in triplicate over 10 seconds and expressed as RLUs (relative light units). Relative light units (RLU) were normalized to the protein content of each sample, determined by BSA protein assay (Pierce, Rockford, Ill.). All the experiments were conducted in triplicate. The results obtained for the transfection of HepaG2 cells with pCMV-luc using the tertiary complexes (containing DNA, anionic polyacetal 10, and polycation 12) are shown in FIG. 2. The results show that tertiary complexes containing polyacetal 10 provided increased transfection efficiency. The results also indicated that the tertiary complexes would be effective for in vivo polynucleotide delivery.

Example 11

Figure 9:
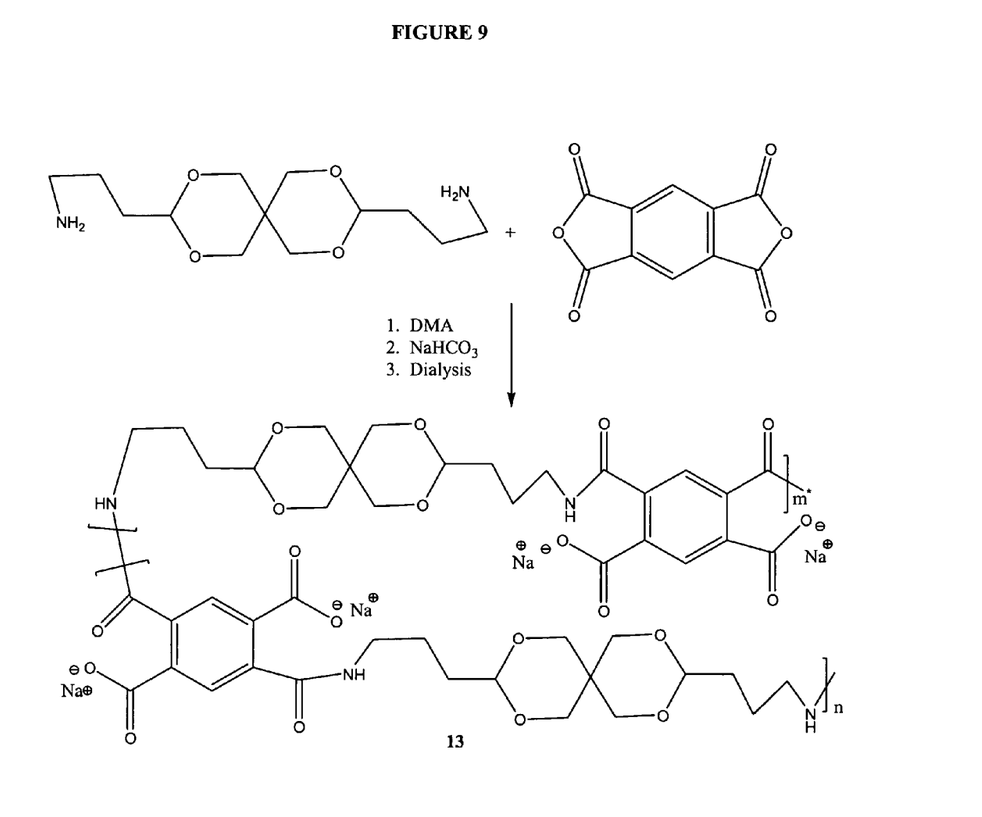
FIG. 9 shows a preferred reaction scheme for the preparation of anionic polyacetal 13 as described in Example 11.

Synthesis of polyacetal 13 (FIG. 9): 1,2,4,5-Benzenetetra-carboxylic dianhydride (5.0 g, 22.9 mmol, Aldrich Chemical Company) was added to a solution of 3,9-bis(3-aminopropyl)-2,4,8,10-tetraoxaspiro[5.5]undecane (6.34 g, 22.9 mmol TCI Chemical Company) in dimethylacetamide (DMA, 100 mL,). The mixture was stirred for 3 days at room temperature. The reaction was quenched with saturated sodium bicarbonate carbonate in water (50 mL). The precipitate was filtered, and the filtrate was poured in acetone (1000 mL) and white precipitate formed. The precipitate was redissolved in distilled water and dialyzed in cellulose membrane (2,000 molecular weight cut-off) in distilled water for 15 hours with 4 times of water changing. Clear solid polyacetal 13 (3.2 g) was obtained after the water was removed by rotary evaporation. The molecular weight of the polyacetal 13 was about 45,000 daltons (by HPSEC, polyethylene glycol standards). $^1H$- and $^{13}C$ NMR spectra of polyacetal 13 were obtained and found to be consistent with the chemical structure of polyacetal 13 shown in FIG. 9. In FIG. 9, n and m are each individually integers in the range of about 1 to about 200. Control over the molecular weight of the polyacetal 13 (and thus over m and n) may be exercised by varying the molar ratio of the dianhydride monomer to the diamine monomer.

Example 12

Sizes and zeta potentials of binary polycation PEI-DNA and biodegradable polycation 12-DNA complexes were determined as follows:

Size Measurements: A series of solutions containing different amounts of polycation PEI or biodegradable polycation 12 (50 µL) in HEPES buffers was added to solutions containing DNA (2 µg, 50 µL) in HEPES buffers by pipetting, agitated by pipetting, then allowed to equilibrate for 1 minute. Particle sizes (nm) of the resulting binary complexes were measured by ZetaPALS, and the results are summarized in Table 1 below.

Zeta potential measurements: Selected different amounts of PEI or polycation 12 were added to a solution of DNA with similar concentrations as in the size measurements but scaled-up to 1.6 mL total volume. Zeta potentials (mV) of the resulting binary complexes were measured by ZetaPALS, and the results are summarized in Table 1 below.

TABLE 1

| | 0.125 | 0.25 | 0.5 | 1 | 2 | 4 | 8 | 16 | 32 | 64 | 128 | 256 | 512 |
|---|---|---|---|---|---|---|---|---|---|---|---|---|---|
| | | | | | Amount of PEI (µg) | | | | | | | | |
| PEI:DNA ratio (w:w) | 0.06 | 0.1 | 0.25 | 0.5 | 1 | 2 | 4 | 8 | 16 | 32 | 64 | 128 | 256 |
| Particle size (nm) | 124.1 | 103 | 153 | 112 | 94.6 | 78.6 | 82.5 | 88.1 | 80.4 | 69 | 55.8 | 63.6 | 91 |
| Zeta potential (mV) | | | −29 | | 49 | | | | | | 51 | | |
| Poly-dispersity | 0.311 | 0.21 | 0.11 | 0.2 | 0.21 | 0.23 | 0.21 | 0.27 | 0.25 | 0.2 | 0.33 | 0.3 | 0.3 |
| Avg. Count Rate (kcps) | 23.9 | 73.4 | 497 | 335 | 203 | 143 | 158 | 167 | 161 | 151 | 169 | 200 | 305 |
| Baseline Index | 0 | 2.7 | 7.8 | 6.5 | 10 | 9.7 | 8.6 | 0 | 0 | 9.8 | 8.2 | 7.2 | 9.9 |

TABLE 1-continued

|  | 0.125 | 0.25 | 0.5 | 1 | 2 | 4 | 8 | 16 | 32 | 64 | 128 | 256 | 512 |
|---|---|---|---|---|---|---|---|---|---|---|---|---|---|
|  | Amount of biodegradable polycation 12 (μg) | | | | | | | | | | | | |
| 12:DNA ratio (w:w) |  | 0.1 | 0.25 | 0.5 | 1 | 2 | 4 | 8 | 16 | 32 | 64 | 128 |  |
| Particle size (nm) |  | 200 | 106 | 110 | 1316 | 91.2 | 88.7 | 80.4 | 77.3 | 74 | 72.8 | 71.3 |  |
| Zeta potential (mV) |  |  |  | −27 | 19 | 38.2 |  |  |  |  |  |  |  |
| Poly-dispersity |  | 0.3 | 0.21 | 0.1 | 0.3 | 0.12 | 0.13 | 0.19 | 0.19 | 0.2 | 0.2 | 0.2 |  |
| Avg. Count Rate (kcps) |  | 18.1 | 61.9 | 227 | 277 | 274 | 259 | 162 | 143 | 126 | 121 | 118 |  |
| Baseline Index |  | 0 | 5.1 | 8.3 | 9.1 | 8.9 | 8.9 | 7.8 | 9.3 | 9.4 | 9.8 | 8.3 |  |

Example 13

Sizes and zeta potentials of tertiary complexes were determined as follows:

Size Measurements: A series of solutions containing different amounts of polyacetal 13 (100 μL) in buffers were added to solutions containing binary PEI and DNA complexes (8 μg and 2 μg, respectively, 100 mL) in HEPES buffers by pipetting, agitated by pipetting, then allowed to equilibrate for 1 minute. Particle sizes (nm) of the resulting ternary complexes were measured by ZetaPals, and the results are summarized in Table 2 below.

Zeta potential measurements: A series of solutions containing different amounts of polyacetal 13 in buffers were added to solutions of binary PEI and DNA complexes with similar concentrations as in the size measurements but scaled-up to 1.6 mL total volume. Zeta potentials (mV) of the resulting ternary complexes were measured by ZetaPals, and the results are summarized in Table 2 below.

TABLE 2

|  | 500 | 250 | 125 | 64 | 32 | 16 |
|---|---|---|---|---|---|---|
|  | Amount of Polyacetal 13 (μg) (HEPES buffer) | | | | | |
| 13:PEI:DNA (w/w) | 500:8:2 | 250:8:2 | 125:8:2 | 64:8:2 | 32:8:2 | 16:8:2 |
| measurement 1 (nm) | 177 | 146 | 138 | 140 | Turbidity | 121 |
| measurement 2 (nm) | 182 | 145 | 137 | 143 | Turbidity | 99 |
| measurement 3 (nm) | 173 | 154 | 136 | 143 | Turbidity | 114 |
| zeta (mV) | −37 | −51 | −28 | −25 |  | 42 |
|  | Amount of Polyacetal 13 (μg) (BIGS buffer)[1] | | | | | |
| 13:PEI:DNA (w/w) | 500:8:2 | 250:8:2 | 125:8:2 | 64:8:2 | 32:8:2 | 16:8:2 |
| measurement 1 (nm) | 183.6 | 170.1 | 148.1 | 150.6 | Turbidity | 157.8 |
| measurement 2 (nm) | 185.2 | 153.0 | 157.5 | 143.0 | Turbidity | 131.2 |
| measurement 3 (nm) | 178.4 | 161.1 | 154.0 | 166.5 | Turbidity | 142.2 |
| zeta (mV) | −34 | −30 | −25 | −32 | −12 | 38 |

[1]BIGS buffers are 10% HEPES, 5% glucose, pH 7.4

Example 14

Safety studies of the polyacetal 13: 15 hairless mice (SKH1 model, 5-6 weeks old, 18-20 grams) were purchased from Charles River Laboratories and were kept at the animal facility for 3 days before conducting experiments. 15 mice were divided into 3 groups (5 mice per group). Polyacetal 13 samples were prepared by dissolving the polymer in PBS (pH 7.4) at three different concentrations: (1) 40 mg/mL, (2) 20 mg/mL, and (3) 10 mg/mL. The mice were then injected (tail vein) with 100 μL of each concentration (one injection per mouse). The mice were observed for 5 hours and results are shown in Table 3 below:

TABLE 3

|  | Polyacetal 13 Dose (μg) | | |
|---|---|---|---|
|  | 1,000 | 2,000 | 4,000 |
| # of animals injected | 5 | 5 | 5 |
| # of animals alive | 5 | 5 | 5 |
| Behavior | Active | Active | Active |

It will be appreciated by those skilled in the art that various omissions, additions and modifications may be made to the processes and compositions described above without departing from the scope of the invention, and all such modifications and changes are intended to fall within the scope of the invention, as defined by the appended claims.

What is claimed is:

1. A complex for delivering a polynucleotide to a cell, comprising:
   a polynucleotide;
   a polycation; and
   an acid-degradable polyanion comprising a recurring unit of Formula (I):

-continued wherein Y is selected from the group consisting of —$(CH_2)_2$—, —$(CH_2)_2$—O—$(CH_2)_2$—, and —$(CH_2)_2$—O—$(CH_2)_2$—O—$(CH_2)_2$—;

wherein W is a targeting ligand selected from the group consisting of galactose, lactose, mannose, transferrin, antibody, antibody fragment, and RGD peptide;

wherein m and n are each individually integers in the range of 1 to 100,000; and wherein Z is selected from the group consisting of Li, Na, K, Rb, Cs, Be, Mg, and Ca.

2. The complex of claim 1 in which the polynucleotide is selected from the group consisting of DNA and RNA.

3. The complex of claim 1 in which the polynucleotide is selected from the group of consisting of plasmid DNA, antisense DNA, DNA oligomer, siRNA, ribozyme, and tetramer.

4. The complex of claim 1 in which the polycation has a weight average molecular weight in the range of about 2,000 daltons to about 50,000 daltons as determined by high pressure size exclusion chromatography.

5. The complex of claim 1 in which the polycation is selected from the group consisting of polyamine, poly(ethylenimine), polyester-polyamine, polyphosphatediester-polyamine, and polyacetal-polyamine.

6. The complex of claim 1 in which the polycation is a biodegradable polycation.

7. The complex of claim 6 in which the biodegradable polycation is selected from the group consisting of polyester-polyamine, polyphosphatediester-polyamine, and polyacetal-polyamine.

8. The complex of claim 1 in which the acid-degradable polyanion comprises an acid-degradable group selected from the group consisting of acetal, imine, hydrazone, enol, enol ether, enamine, ketal, and oxime.

9. A method of making the complex of claim 1, comprising:
    intermixing a first solution comprising the acid-degradable polyanion with a second solution comprising the polycation and the polynucleotide.

10. A method of delivering the complex of claim 1 into a cell comprising contacting the complex of claim 1 with a cell.

11. The method of claim 10 in which the cell is a mammalian cell.

12. The method of claim 11 in which the contacting of the complex with the cell is conducted by introducing the complex into the body of a mammal.

13. The method of claim 12 in which the introducing of the complex into the body of the mammal is conducted by systemic administration.

14. The method of claim 12 in which the introducing of the complex into the body of the mammal is conducted by local administration.

* * * * *

UNITED STATES PATENT AND TRADEMARK OFFICE
CERTIFICATE OF CORRECTION

| | | |
|---|---|---|
| PATENT NO. | : 7,794,696 B2 | Page 1 of 1 |
| APPLICATION NO. | : 10/946383 | |
| DATED | : September 14, 2010 | |
| INVENTOR(S) | : Van et al. | |

It is certified that error appears in the above-identified patent and that said Letters Patent is hereby corrected as shown below:

At Column 5, Line 27, before "group" please insert --the--;

At Column 8, Line 53 (Approx.), change "gl" to --µl--.

Signed and Sealed this
Twenty-seventh Day of November, 2012

David J. Kappos
*Director of the United States Patent and Trademark Office*